United States Patent [19]
Edwards

[11] Patent Number: 5,968,041
[45] Date of Patent: Oct. 19, 1999

[54] DIRECTABLE THERMAL ENERGY DELIVERY APPARATUS

[75] Inventor: Stuart D. Edwards, Portola Valley, Calif.

[73] Assignee: Vida Care, Inc., Sunnyvale, Calif.

[21] Appl. No.: 09/054,030

[22] Filed: Apr. 2, 1998

[51] Int. Cl.⁶ .................................................. A61B 17/39
[52] U.S. Cl. ............................ 606/41; 606/49; 607/101; 607/98
[58] Field of Search ................................. 606/41, 42, 45, 606/46, 48–50; 607/98–102, 104–105, 122

[56] References Cited

U.S. PATENT DOCUMENTS

| | | | |
|---|---|---|---|
| 5,269,780 | 12/1993 | Roos | 606/42 |
| 5,401,272 | 3/1995 | Perkins | 606/15 |
| 5,536,267 | 7/1996 | Edwards et al. | 606/41 |
| 5,782,827 | 7/1998 | Gough et al. | 606/41 |
| 5,799,715 | 7/1998 | Tu | 606/108 |
| 5,810,804 | 9/1998 | Gough et al. | 606/41 |

*Primary Examiner*—Linda C. M. Dvorak
*Assistant Examiner*—Roy Gibson
*Attorney, Agent, or Firm*—Wilson Sonsini Goodrich & Rosati

[57] ABSTRACT

A cell necrosis apparatus includes an introducer with a tissue piercing distal end. An RF electrode device includes a first RF electrode with a tissue piercing distal end, a second RF electrode with a tissue piercing distal end, and a third RF electrode with a tissue piercing distal end. The first and second electrodes each have an exterior non-insulated energy delivery surface and an exterior opposing insulated surface. The first, second and third RF electrodes are deployable from the introducer with the first and second RF electrodes exterior non-insulated energy delivery surfaces facing and surrounding the third RF electrode.

28 Claims, 5 Drawing Sheets

DIRECTABLE THERMAL ENERGY DELIVERY APPARATUS

BACKGROUND OF THE INVENTION

1. Field of the Invention

This invention relates generally to an RF treatment apparatus, and more particularly to an RF treatment apparatus operable in bipolar or monopolar modes to deliver directable thermal energy to a target tissue site.

2. Description of Related Art

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

High frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated. The frequency of the current for this use must be above ca. 300 kHz in order to avoid adverse nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radio frequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radio frequency electrode or microwave antenna through a duct to the zone of treatment and apply energy diffusely through the duct wall into the surrounding tissue in all directions.

Current open procedures for treatment of target tissues are extremely disruptive and cause a great deal of damage to healthy tissue. Accordingly, there has recently been a fair amount of emphasis of minimally invasive procedures for target tissue destruction and removal.

Among the problems associated with all of these procedures is the requirement that highly localized heat be produced at depths of several centimeters beneath the surface of the body. Certain techniques have been developed with microwave radiation and ultrasound to focus energy at various desired depths. RF applications may be used at depth during surgery. However, the extent of localization is generally poor with the result that healthy tissue may be harmed. Induction heating gives rise to poor localization of the incident energy as well. Although induction heating may be achieved by placing an antenna on the surface of the body, superficial eddy currents are generated in the immediate vicinity of the antenna when it is driven using RF current, and unwanted surface heating occurs with little coupled to the underlying tissue. Thus, noninvasive procedures for providing heat to internal target tissue sites have had difficulties is substantial specific and selective treatment.

Hyperthermia, which can be from an RF or microwave source, applied heat to tissue but does not exceed 45 degrees C. so that normal cells survive. In thermotherapy, heat energy of greater than 45 degrees C. is applied, resulting in histological damage and the denaturization of proteins. Hyperthermia has been applied more recently for cell necrosis of a target tissue site. In hyperthermia, it is desirable to induce a state of hyperthermia that is localized by interstitial current heating to a specific area while concurrently insuring minimum thermal damage to healthy surrounding tissue. Often, the target tissue site is located subcutaneously and addressing the target tissue site requires either surgery, endoscopic procedures or exits healing requires either surgery, endoscopic procedures or external radiation. It is difficult to externally induce hyperthermia in deep body tissue because current density is diluted due to its absorption by healthy tissue. Additionally, a portion of the RF energy is reflected at the muscle/fat and bone interfaces which adds to the problem of depositing a known quantity of energy directly on a small target tissue site.

There is a need for an RF treatment apparatus to minimally invasively create cell necrosis in a target tissue site. There is a further need for an RF treatment apparatus that provides directional delivery of RF energy to a target tissue site. Another need exists for an RF ablation apparatus which can be operated in bipolar or monopolar modes to deliver directable thermal energy to a targeted tissue site.

SUMMARY OF THE INVENTION

Accordingly, an object of the invention is to provide a cell necrosis apparatus that creates cell necrosis in a target tissue site.

Another object of the invention is to provide an RF treatment apparatus that provides directional delivery of RF energy to a target tissue site.

A further object of the invention is to provide an RF ablation apparatus which can be operated in bipolar or monopolar modes to deliver directable thermal energy to a target tissue site.

These and other advantages are achieved in a cell necrosis apparatus that includes an introducer with a tissue piercing distal end. An RF electrode device includes a first RF electrode with a tissue piercing distal end, a second RF electrode with a tissue piercing distal end, and a third RF electrode with a tissue piercing distal end. The first and second electrodes each have an exterior non-insulated energy delivery surface and an exterior opposing insulated surface. The first, second and third RF electrodes are deployable from the introducer with the first and second RF electrodes exterior non-insulated energy delivery surfaces facing and surrounding the third RF electrode.

DETAILED DESCRIPTION

Figure 1:
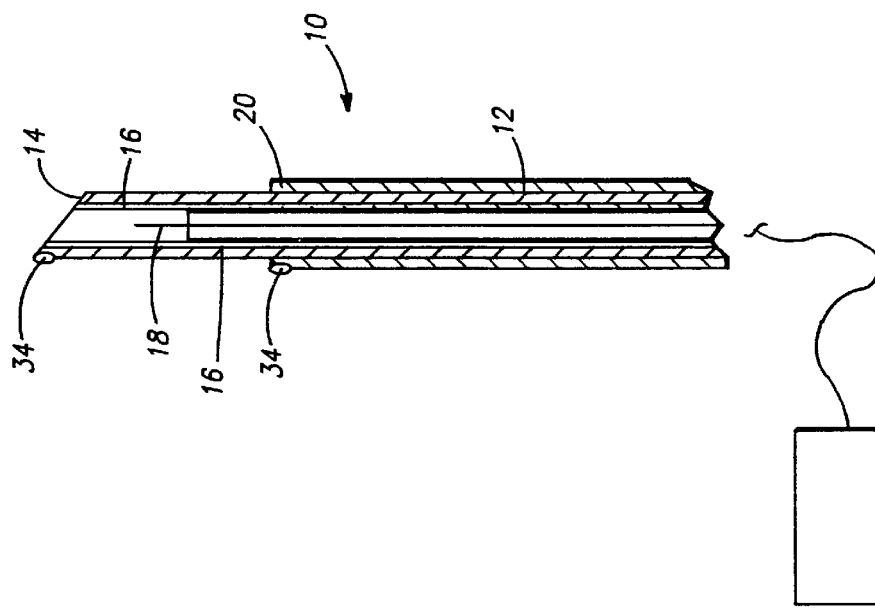
FIG. 1 is a cross-sectional view of one embodiment of a cell necrosis apparatus of the present invention.

As shown in FIG. 1, a cell necrosis apparatus 10 includes a flexible, semi-flexible or rigid introducer 12. Introducer 12 has a tissue piercing distal end. An RF electrode device is positionable in introducer 12 as introducer 12 is advanced through tissue. RF electrode device includes first and second RF electrodes 16 and a third RF electrode 18. Electrodes 16 are positioned in introducer 12 in non-deployed states. Each electrode 16 and 18 has a tissue piercing distal end. Cell necrosis apparatus 10 can includes more than two electrodes 16 and more than two electrodes 18. An infusion medium can be introduced through introducer 12, RF electrode 16 or RF electrode 18. A suitable infusion medium can be an electrolytic solution, a disinfectant, a chemotherapeutic agent, and the like.

An insulation sleeve 20 can be positioned around an exterior of introducer 12. Any portion of introducer 12 not covered by insulation sleeve 20 can provide an RF electrode surface. In one embodiment, a distal portion of introducer 12 is not covered by insulation sleeve and when coupled to an RF generator 22 becomes an RF electrode. Electrodes 16 and 18 are coupled to RF generator 22.

Electrodes 16 and 18 can be made of a variety of conductive materials, both metallic and non-metallic. One suitable material is type 304 stainless steel of hypodermic quality. In some applications, all or a portion of secondary electrode 16 can be made of a shaped memory metal, such as NiTi, commercially available from Raychem Corporation, Menlo Park, Calif.

Electrodes 16 and 18 can have different lengths. The lengths can be determined by the actual physical length of an electrode 16 or 18 and not covered by an insulator. Suitable lengths include but are not limited to 17.5 cm., 25.0 cm. and 30.0 cm. The actual length of an electrode 16 and 18 depends on the location of the selected tissue mass to be ablated, its distance from the skin, its accessibility as well as whether or not the physician chooses a laparoscopic, percutaneous or other procedure. Insulation sleeve 20 can be made of a polyamide material and may be semi-rigid.

Figure 2:
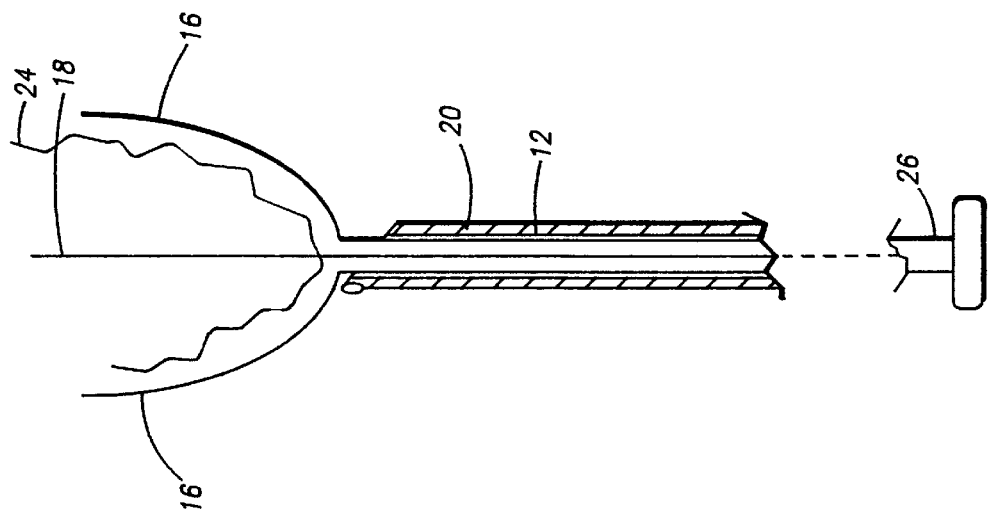
FIG. 2 illustrates the deployment of RF electrodes from the introducer of the apparatus shown in FIG. 1.

Referring now to FIG. 2, electrodes 16 and 18 are shown advanced from introducer 12 in deployed configurations which provides an ability to create an ablation volume that is larger than the cross-sectional diameter of introducer 12. Electrodes 16 and/or 18 can be pre-sprung in order to be advanced in the expanded deployed state. Alternatively, electrodes 16 and/or 18 can be made of a shaped memory metal or other material which achieves the expanded deployed state. In one embodiment, electrodes 16 are deployed to surround electrode 18. In this embodiment, electrode 18 is deployed with less curvature than electrodes 16. In another embodiment, electrode 18 is deployed with minimal, if any, curvature from introducer 18 and extends through a center of a targeted tissue mass.

When introducer 12 has been positioned at a selected tissue site, including but not limited to a solid lesion, RF electrodes 16 are deployed in the expanded state to surround a targeted cell necrosis tissue site 24. Electrodes 16 are generally positioned at an exterior of tissue site 24 while electrode 18 is positioned in an interior of tissue site 24. An electrode advancement and retraction member 26 is coupled to electrodes 16 and 18. Volumetric cell necrosis is created between electrodes 16 and 18. Alternatively, electrodes 16 need not be deployed around an exterior of tissue site 24.

Figure 4:
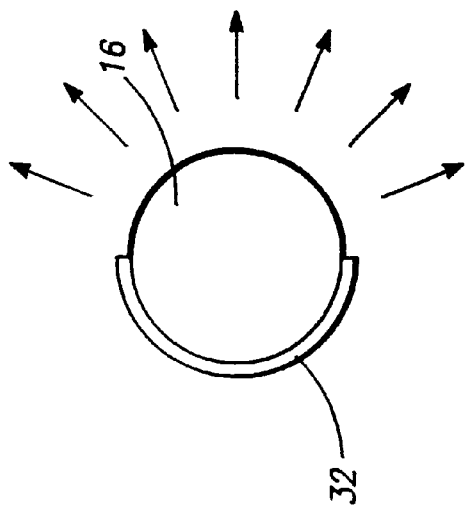
FIG. 4 is a cross-sectional view of a partially insulated electrode shown in FIG. 3.
Figure 3:
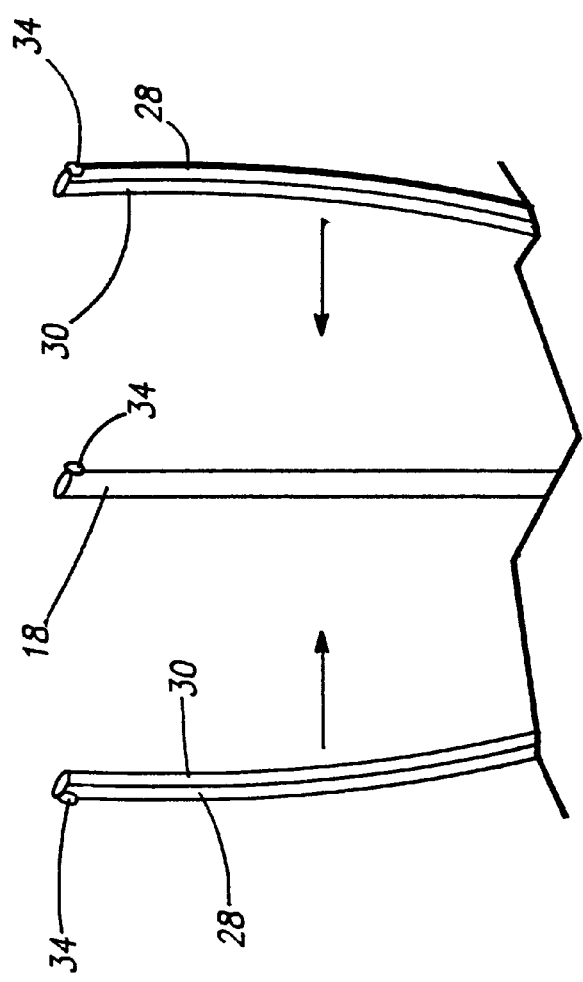
FIG. 3 illustrates the insulated and non-insulated sections of some of the RF electrodes of the apparatus shown in FIG. 1.

Referring now to FIGS. 3 and 4, electrodes 16 each have an insulated section 28 and a non-insulated section 30. Insulated sections 28 include an insulation layer 32. Non-insulated sections 30 provide energy delivery surfaces that are directed to tissue site 24, particularly to its center. Electrode 18 remains substantially un-insulated. A bipolar deliver of electromagnetic energy occurs between electrode 18 and non-insulated sections 30. This results in the creation of a predictable and directable cell necrosis volume.

One or more sensors 34 may be positioned on at least a portion of interior or exterior surfaces of introducer 12, electrodes 16 and 18 and/or insulation sleeve 20. Preferably, sensors 34 are positioned at distal ends of introducer 12, electrodes 16 and 18 and insulation sleeve 20. Sensors 34 permit accurate measurement of temperature at a tissue site in order to determine, (i) the extent of cell necrosis, (ii) the amount of cell necrosis, (iii) whether or not further cell necrosis is needed and (iv) the boundary or periphery of the ablated mass. Further, sensors 34 prevent non-targeted tissue from being destroyed or ablated.

Sensors 34 are of conventional design, including but not limited to thermistors, thermocouples, resistive wires, and the like. Suitable thermal sensors 34 include a T type thermocouple with copper constantene, J type, E type, K type, fiber optics, resistive wires, thermocouple IR detectors, and the like. It will be appreciated that sensors 34 need not be thermal sensors.

Sensors 34 are used measure temperature and/or impedance to permit monitoring and controlled delivery of energy. Sensors 34 permit a desired level of cell necrosis to be achieved without destroying non-target sites. This reduces damage to tissue surrounding the targeted mass to be ablated. By monitoring the temperature and/or impedance at various points within the interior of a selected tissue mass, a determination of the selected tissue mass periphery can be made, as well as a determination of when cell necrosis is complete. If at any time sensors 34 determine that a desired cell necrosis temperature is exceeded, then an appropriate feedback signal is received at RF generator 22 which then regulates the amount of electromagnetic energy delivered to electrodes 16 and 18.

Introducer 12 can be moved up and down, rotated about its longitudinal axis, and moved back and forth, in order to define, along with sensors, the periphery or boundary of the selected tissue mass, including but not limited to a tumor. This permits a wade variety of different cell necrosis geometries to be created including but not limited to spherical, semi-spherical, spheroid, triangular, semi-triangular, square, semi-square, rectangular, semi-rectangular, conical, semi-conical, quadrilateral, semi-quadrilateral, semi-quadrilateral, rhomboidal, semi-rhomboidal, trapezoidal, semi-trapezoidal, combinations of the preceding, geometries with non-planar sections or sides, free-form and the like.

Figure 5:
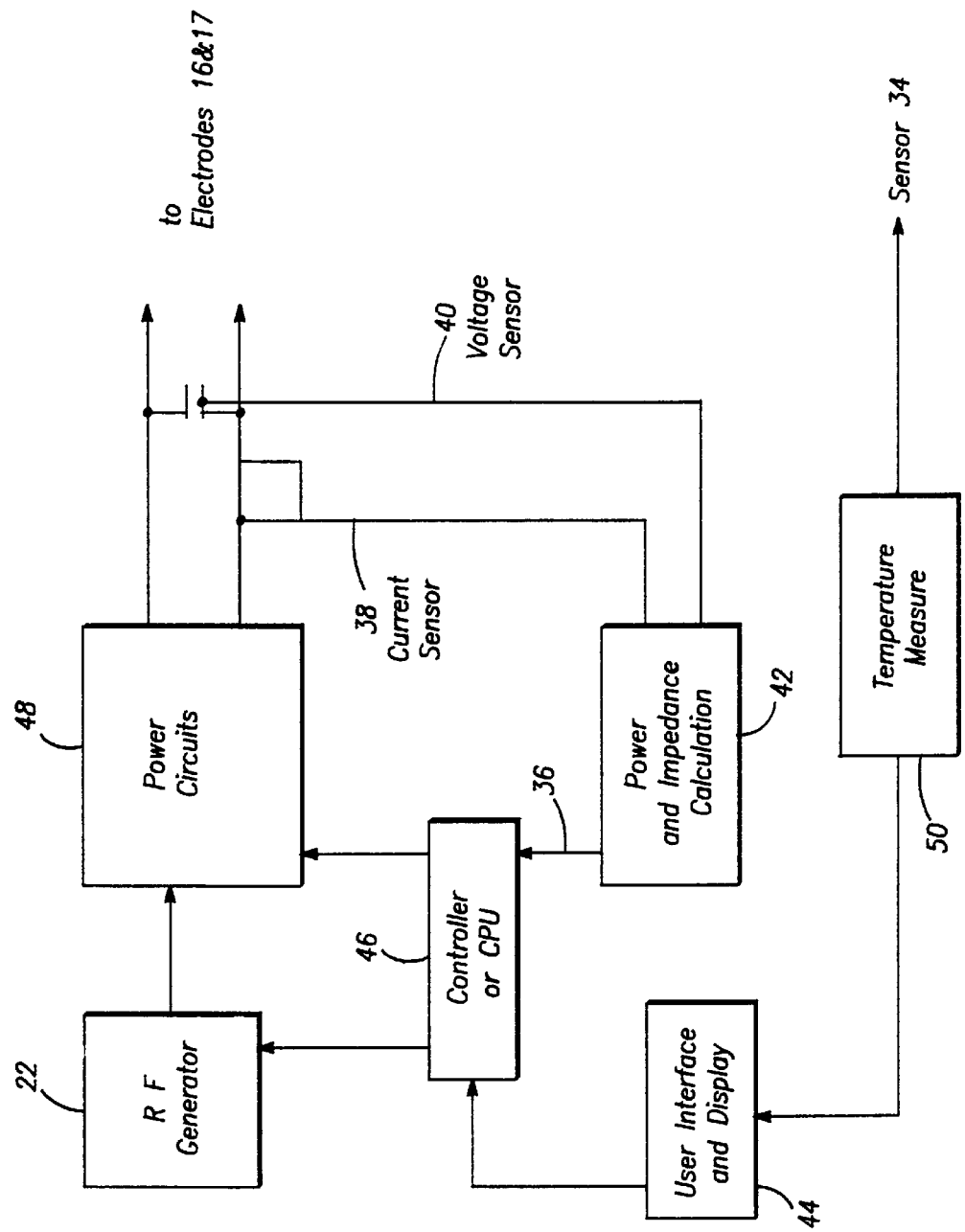
FIG. 5 is a block diagram of a feedback control system useful with the methods of the present invention.
Figure 6:
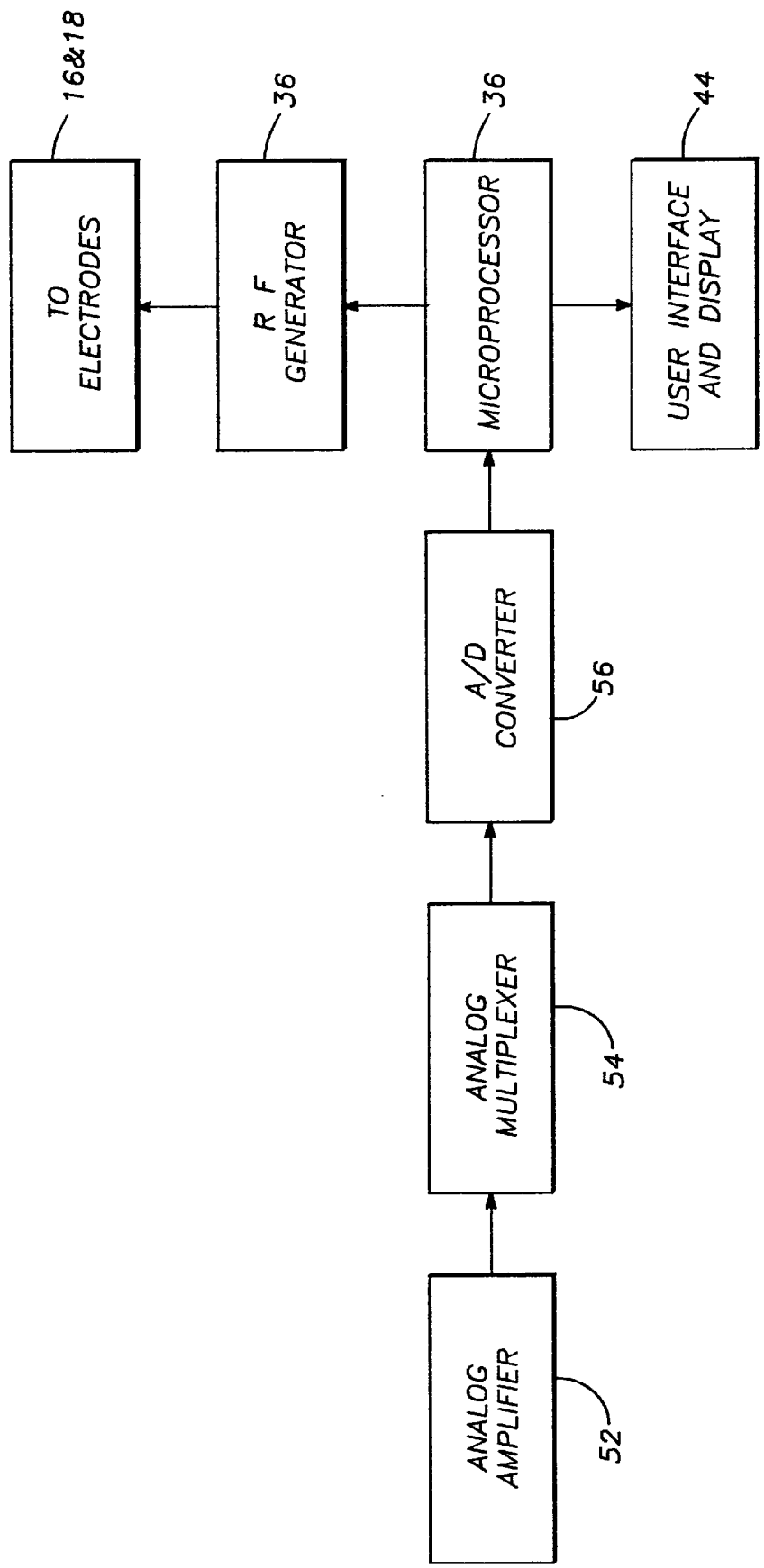
FIG. 6 is a block diagram illustrating an analog amplifier, analog multiplexer and microprocessor used with the feedback control system of FIG. 5.

Referring now to FIGS. 5 and 6, an open or closed loop feedback system couples sensors 34 to RF generator 22. The temperature of the tissue, or of electrodes 16 and/or 18 is monitored, and the output power of RF generator 22 adjusted accordingly. The physician can, if desired, override the closed or open loop system. A microprocessor can be included and incorporated in the closed or open loop system to switch power on and off, as well as modulate the power. The closed loop system utilizes a microprocessor 36 to serve as a controller, watch the temperature, adjust the RF power, look at the result, refeed the result, and then modulate the power.

With the use of sensors 34 and the feedback control system a tissue adjacent to RF electrodes 16 and 18 can be maintained at a desired temperature for a selected period of time without impeding out. Each RF electrode 16 and 18 is connected to resources which generate an independent output for each RF electrode 16 and 18. An output maintains a selected energy at RF electrodes 16 and 18 for a selected length of time.

Current delivered through RF electrodes 16 and 18 is measured by current sensor 38. Voltage is measured by voltage sensor 40. Impedance and power are then calculated at power and impedance calculation device 42. These values can then be displayed at user interface and display 44. Signals representative of power and impedance values are received by a controller 46.

A control signal is generated by controller 46 that is proportional to the difference between an actual measured value, and a desired value. The control signal is used by power circuits 48 to adjust the power output in an appropriate amount in order to maintain the desired power delivered at respective RF electrodes 16 and 18.

In a similar manner, temperatures detected at sensors 34 provide feedback for maintaining a selected power. The actual temperatures are measured at temperature measurement device 50, and the temperatures are displayed at user interface and display 44. A control signal is generated by controller 46 that is proportional to the difference between an actual measured temperature, and a desired temperature. The control signal is used by power circuits 48 to adjust the power output in an appropriate amount in order to maintain the desired temperature delivered at the respective sensor. A multiplexer can be included to measure current, voltage and temperature, at the numerous sensors 34, and energy can be delivered to RF electrodes 16 and 18 in monopolar or bipolar fashion.

Controller 46 can be a digital or analog controller, or a computer with software. When controller 46 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 44 includes operator controls and a display. Controller 46 can be coupled to imaging systems, including but not limited to ultrasound, CT scanners, X-ray, MRI, mammographic X-ray and the like. Further, direct visualization and tactile imaging can be utilized.

The output of current sensor 38 and voltage sensor 40 is used by controller 46 to maintain a selected power level at RF electrodes 16 and 18. The amount of RF energy delivered controls the amount of power. A profile of power delivered can be incorporated in controller 46, and a preset amount of energy to be delivered can also be profiled.

Circuitry, software and feedback to controller 46 result in process control, and the maintenance of the selected power that is independent of changes in voltage or current, and are used to change, (i) the selected power, (ii) the duty cycle (on-off and wattage), (iii) bipolar or monopolar energy delivery, and (iv) infusion medium delivery, including flow rate and pressure. These process variables are controlled and varied, while maintaining the desired delivery of power independent of changes in voltage or current, based on temperatures monitored at sensors 34.

Current sensor 38 and voltage sensor 40 are connected to the input of an analog amplifier 52. Analog amplifier 52 can be a conventional differential amplifier circuit for use with sensors 34. The output of analog amplifier 104 is sequentially connected by an analog multiplexer 54 to the input of A/D converter 56. The output of analog amplifier 52 is a voltage which represents the respective sensed temperatures. Digitized amplifier output voltages are supplied by A/D converter 56 to microprocessor 36. Microprocessor 36 may be a type 68HCII available from Motorola. However, it will be appreciated that any suitable microprocessor or general purpose digital or analog computer can be used to calculate impedance or temperature.

Microprocessor 36 sequentially receives and stores digital representations of impedance and temperature. Each digital value received by microprocessor 36 corresponds to different temperatures and impedances.

Calculated power and impedance values can be indicated on user interface and display 44. Alternatively, or in addition to the numerical indication of power or impedance, calculated impedance and power values can be compared by microprocessor 36 with power and impedance limits. When the values exceed predetermined power or impedance values, a warning can be given on user interface and display 96, and additionally, the delivery of RF energy can be reduced, modified or interrupted. A control signal from microprocessor 36 can modify the power level supplied by RF generator 22.

Figure 7:
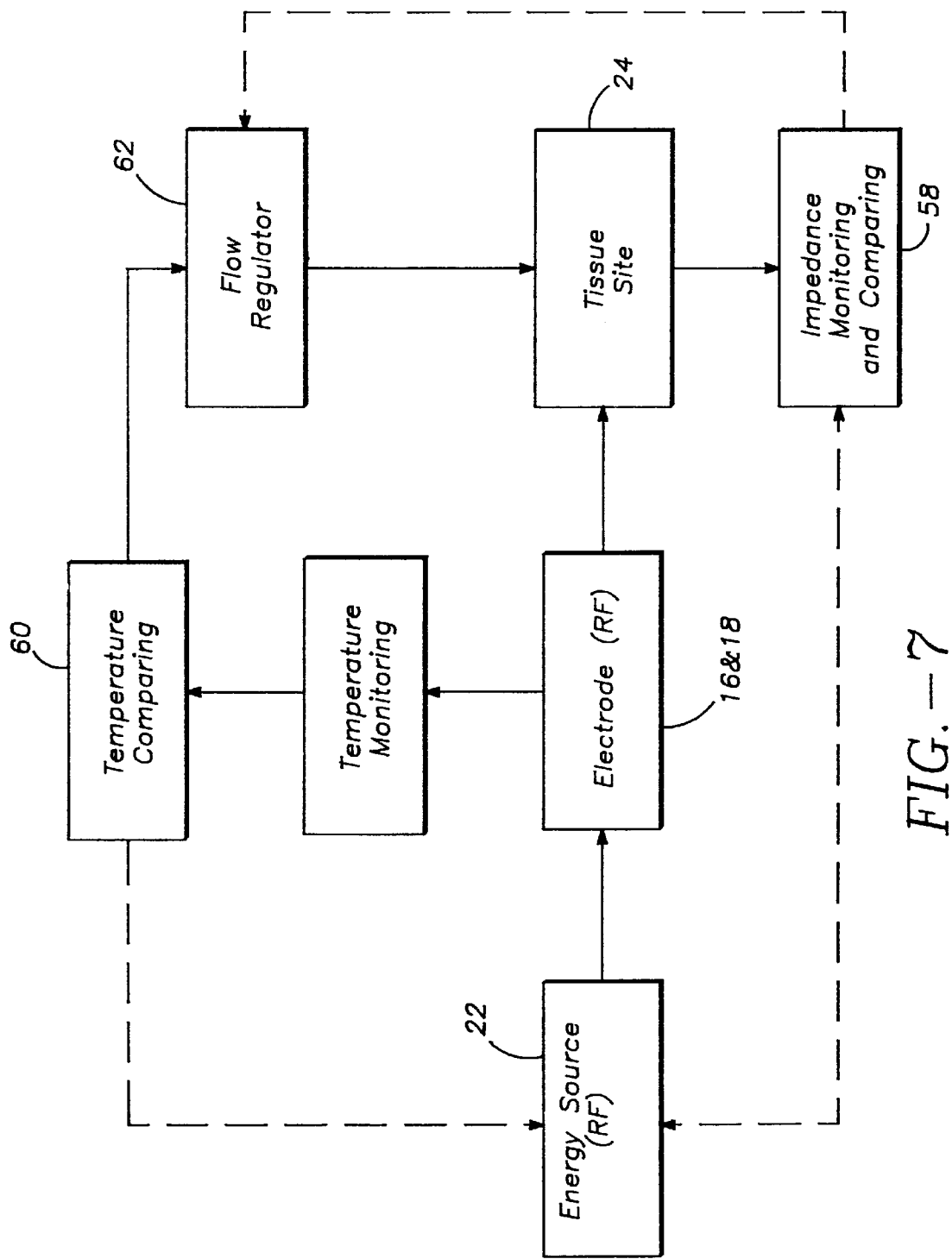
FIG. 7 is a block diagram of a temperature/impedance feedback system that can be used to control an infusion medium flow rate through the apparatus of FIG. 1.

FIG. 7 illustrates a block diagram of a temperature/impedance feedback system that can be used to control an infusion medium flow rate through introducer 12, RF electrodes 16 and/or 18. Electromagnetic energy is delivered to electrodes 16 and 18 by RF generator 22, and applied to tissue site 24. An impedance monitor 58 can be used to ascertain tissue impedance, based on the energy delivered to tissue, and compares the measured impedance value to a set value. If the measured impedance exceeds the set value a disabling signal is transmitted to RF generator 22, ceasing further delivery of energy to electrodes 16 and 18. If measured impedance is within acceptable limits, energy continues to be applied to the tissue. During the application of energy to the tissue sensor 34 measures the temperature of the tissue. A comparator 60 receives a signal representative of the measured temperature and compares this value to a pre-set signal representative of the desired temperature. Comparator 60 sends a signal to a flow regulator 62 representing a need for a higher flow rate of the infusion medium.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A cell necrosis apparatus, comprising:

an introducer with a tissue piercing distal end;

an RF electrode device including a first RF electrode with a tissue piercing distal end; a second RF electrode with a tissue piercing distal end, and a third RF electrode with a tissue piercing distal end, the first and second electrodes each having an exterior non-insulated energy delivery surface and an exterior opposing insulated surface, the first, second and third RF electrodes being deployed from the introducer with the first and second RF electrodes exterior non-insulated energy delivery surfaces facing and surrounding the third RF electrode.

2. The apparatus of claim 1, further comprising:

an insulation sleeve in a surrounding relationship to at least a portion of the introducer.

3. The apparatus of claim 1, further comprising:

an electrode advancement member coupled to the RF electrode device.

4. The apparatus of claim 1, wherein the first electrode includes a hollow lumen configured to deliver a media to a selected tissue site.

5. The apparatus of claim 1, wherein the third electrode includes a hollow lumen configured to deliver a media to a selected tissue site.

6. The apparatus of claim 1, wherein the introducer is configured to deliver a media to a selected tissue site.

7. The apparatus of claim 1, wherein the first and second and RF electrodes are configured to be deployed from the introducer to surround a selected tissue site and the third RF electrode is configured to be deployed at least partially through the selected tissue site, wherein the first and second RF electrode exterior non-insulated energy delivery surfaces face the selected tissue site.

8. The apparatus of claim 1, further comprising:

a sensor coupled to one of the first RF electrode, the second RF electrode, the third RF electrode or the introducer.

9. The apparatus of claim 8, further comprising:

a feedback control system coupled to the sensor and to an RF energy source.

10. The apparatus of claim 1, wherein the first and second RF electrodes are made of stainless steel.

11. The apparatus of claim 1, wherein the first and second RF electrodes are made of a shaped memory alloy.

12. The apparatus of claim 1, wherein the first and second RF electrodes are preformed to a selected geometric configuration.

13. The apparatus of claim 1, wherein the first and second RF electrodes operate in a bipolar mode.

14. The apparatus of claim 13, wherein the third RF electrode operates in a monopolar mode.

15. A cell necrosis apparatus, comprising:

an introducer with a tissue piercing distal end;

an RF electrode device including a first RF electrode with a tissue piercing distal end; a second RF electrode with a tissue piercing distal end a third RF electrode with a tissue piercing distal end, and a fourth RF electrode with a tissue piercing distal end, the first, second and third electrodes each having an exterior non-insulated energy delivery surface and an exterior opposing insulated surface, the first, second, third and fourth RF electrodes being deployed from the introducer with the first, second and third RF electrodes exterior non-insulated energy delivery surfaces facing and surrounding the fourth RF electrode.

16. The apparatus of claim 15, further comprising:

an insulation sleeve in a surrounding relationship to at least a portion of the introducer.

17. The apparatus of claim 15, further comprising: an electrode advancement member coupled to the RF electrode device.

18. The apparatus of claim 15, wherein the first electrode includes a hollow lumen configured to deliver a media to a selected tissue site.

19. The apparatus of claim 15, wherein the third electrode includes a hollow lumen configured to deliver a media to a selected tissue site.

20. The apparatus of claim 15, wherein the introducer is configured to deliver a media to a selected tissue site.

21. The apparatus of claim 15, wherein the first, second and third RF electrodes are configured to be deployed from the introducer to surround a selected tissue site and the fourth RF electrode is configured to be deployed at least partially through the selected tissue site, wherein the first, second and third RF electrode exterior non-insulated energy delivery surfaces face the selected tissue site.

22. The apparatus of claim 15, further comprising:

a sensor coupled to one of the first RF electrode, the second RF electrode, the third RF electrode, the fourth electrode or the introducer.

23. The apparatus of claim 22, further comprising: a feedback control system coupled to the sensor and to an RF energy source.

24. The apparatus of claim 15, wherein the first, second and third RF electrodes are made of stainless steel.

25. The apparatus of claim 15, wherein the first, second and third RF electrodes are made of a shaped memory alloy.

26. The apparatus of claim 15, wherein the first, second and third RF electrodes are preformed to a selected geometric configuration.

27. The apparatus of claim 15, wherein the first, second and third RF electrodes operate in a bipolar mode.

28. The apparatus of claim 27, wherein the fourth RF electrode operates in a monopolar mode.

* * * * *